US005606020A

United States Patent [19]
Watanabe et al.

[11] Patent Number: 5,606,020
[45] Date of Patent: Feb. 25, 1997

[54] 6 (R)-L-ERYTHRO-5,6,7,8-TETRAHYDROBIOPTERIN RECEPTOR

[75] Inventors: Yasuyoshi Watanabe; Yumiko Watanabe; Hiroshi Morii, all of Osaka; Toshio Hayashi, Kanagawa-ken, all of Japan

[73] Assignees: Suntory Limited; Osaka Bioscience Institute, both of Osaka, Japan

[21] Appl. No.: 87,802

[22] PCT Filed: Nov. 16, 1992

[86] PCT No.: PCT/JP92/01496

§ 371 Date: Jul. 15, 1993

§ 102(e) Date: Jul. 15, 1993

[87] PCT Pub. No.: WO92/10550

PCT Pub. Date: May 27, 1993

[30] Foreign Application Priority Data

Nov. 16, 1991 [JP] Japan ................................. 3-300894

[51] Int. Cl.$^6$ .................................................. C07K 14/47
[52] U.S. Cl. .................................... 530/350; 530/422
[58] Field of Search ...................................... 530/350, 422

[56] References Cited

PUBLICATIONS

Chemical Abstracts, vol. 115, No. 19, Nov. 11, 1991; Bailey et al: "Role of C6 Chirality of tetrahydropterin cofactor in catalysis and regulation of tyrosine and phenylalanine hydroxylases", Abs. No. 201845x, 2nd pt., p. 443.
Chemical Abstracts, vol. 115, No. 19, Nov. 11, 1991; Ichikawa et al: :"Expression of mouse tyrosine hydroxylase in *Escherichia coli*", Abs. No. 2002245, 1st pt., p. 290.
Miwa et al., Nippon Yakurigaku Zasshi, vol 100(5), Nov. 1992, pp. 367–381. (Translated).
Miwa, Burein Saiensu Kenkyu Hokokushu, vol 5, pp. 83–93, 1992. (Translated).
Harris et al., "Protein Purification Methods", 1RL Press, 1989, pp. 59–64 and 87–97.
Koshimura et al., The 6R-L erythrotetrahydropbiopterin receptor for regulation of dopamine release studied by brain microdialysis, The Japanese Journal of Pharmacology, vol. 52, No. Sup. I, 1990, p. 76P.
Watanabe et al., Molecular mechanisms of tetrahydrobiopterin action on neurotransmitter release, Pteridines, vol. 3, No. 1–2, 1992, pp. 63–64.
Miwa et al., A novel function of tetrahydrobiopterin, Nippon Yakurigaku Zasshi, vol. 100, No. 5, Nov. 1992, pp. 367–381.
Soichi, Miwa "6R–L–Erythro–5,6,7,8–tetrahydrobiopterin receptor . . . ", Burein Saiensu Kenkyn Hokokushu, vol. 5, pp. 83–93, 1992; Ca 118(7):163975r.
Soichi, Miwa et al., "A novel function of tetrahydropioptein," Folia Pharmacological Japonica, vol 100(5), pp. 367–381 (1992), EMBASE An:93 010881.
Watanabe, Y. et al., "Tetrahydiobiopterin and dopamine release", Jpn J. Psychiatry Neurol., vol 45(2), pp. 513–514, 1991 Medline An: 92106606.

*Primary Examiner*—Chhaya D. Sayala
*Attorney, Agent, or Firm*—Cushman Darby & Cushman IP Group of Pillsbury Madison & Sutro LLP

[57] ABSTRACT

A receptor (binding protein) specific for 6(R)-L-erythro-5,6,7,8-tetrahydrobiopterin which is a drug effective for neuropsychiatric disorders such as infantile autism is provided. This receptor is contained in the cytosol fraction or the membrane fraction obtained from a homogenate of an animal organ. It is solubilized from the membrane fraction in the presence of 3-{(3-cholamidopropyl)-dimethylammonio}-1-propanesulfonate (CHAPS). This receptor is characterized in that the binding ability thereof to 6R-BH4 is mostly lost by heating at 100° C. for 10 minutes, the binding ability thereof to 6R-BH4 is significantly lost by incubating with trypsin at 37° C. for 15 minutes, and said receptor shows a relative molecular weight of about 340 to 380 kilodaltons when specifically bound to tritium-labeled 6R-BH4 and analyzed with a molecular sieve provided with a COSMOSIL 5 Diol-300 column.

4 Claims, 5 Drawing Sheets

Fig. 1

HPLC: WHATMAN PARTISIL 10 SCX, 4.6 × 250mm
30 mM AMMONIUM ACETATE, pH 3.5
0.1 mM ASCORBIC ACID
0.1 mM CYSTEINE
1.2 ml/min    DETECTION : OD 265

P2 FRACTION

SPECIFIC BINDING OF [6-³H] 6R—BH4 (fmol/mg PROTEIN)

Fig. 3(b)

CYTOSOL FRACTION

SPECIFIC BINDING OF [6-³H] 6R—BH4 (fmol/mg PROTEIN)

6 (R)-L-ERYTHRO-5,6,7,8-TETRAHYDROBIOPTERIN RECEPTOR

FIELD OF THE INVENTION

This invention relates to a receptor which is specific for 6(R)-L-erythro-5,6,7,8-tetrahydrobiopterin which will hereinafter sometimes be referred to as 6R-BH4 while the one labeled with tritium at the 6-position will sometimes be referred to as [6-$^3$H]6R-BH4. More specifically, the invention relates to a 6R-BH4 receptor which is useful; as a tool in studying biochemical cellular reactions in response to 6R-BH4 binding to the cells; as a tool in searching for and developing agonists of the 6R-BH4 actions on the central nervous and immunological systems or antagonists capable of interrupting these actions when said search and development are conducted on the basis of the biochemical cellular reactions in response to 6R-BH4 binding to the cells and various other natures concerning the binding ability of 6R-BH4; and also as a diagnostic or therapeutic drug for diseases which are attributable to 6R-BH4.

BACKGROUND OF THE INVENTION

6R-BH4 is known to be a common coenzyme for tyrosine hydroxylase and tryptophan hydroxylase which are rate-limiting enzymes in the biosynthesis of neurotransmitters such as dopamine and serotonin. It is considered that 6R-BH4 is a regulating factor in the biosynthesis of these neurotransmitter amines since 6R-BH4 is contained in nerve endings only in an amount which is approximately the Km value of each hydroxylase. In fact, a shortage or decrease in enzymes which participate in the biosynthesis of this coenzyme from GTP will give rise to a decrease in neurotransmitter amines, thus resulting in various neuropsychiacric diseases. Actually, malignant phenylketonuria was discovered in 1974 and subsequent studies have revealed that autopsied brain specimens and cerebrospinal fluid of patients with Parkinson's disease and Alzheimer's dementia show a decrease In 6R-BH4 content. It has also been found that supplementation therapy by 6R-BH4 is effective in the treatment of malignant phenylketonurla, juvenile Parkinson's disease and, in accordance with recent studies, infantile autism of the dysbolism type. Based on these facts, over a hundred 6R-BH4 derivatives have been drug-designed in Switzerland, the United States and Japan and screened for their coenzyme action analogous to 6R-BH4. However, there has not been discovered any derivative which is superior to 6R-BH4 in terms of its action. In addition, no finding has been made hitherto relating to the biochemical cellular responses of 6R-BH4.

DISCLOSURE OF THE INVENTION

Our recent studies have resulted in a novel finding which demands a great change in the concepts relying on previous knowledge.

That is to say, it has been discovered that 6R-BH4 enhances the release and liberation of neurotransmitter amines such as dopamine (DA), norepinephrine and serotonin, and that it also enhances the liberation of glutamir acid, aspartic acid or γ-aminobutyric acid (GABA) via DA and the release of acetylcholine via serotonin. On the other hand, it has been also discovered that when the endogenous 6R-BH4 level is lowered by inhibiting the biosynthesis of 6R-BH4, the DA level per se is not significantly changed whereas the release of DA is suppressed to 50 or lower.

These findings suggest that the endogenous 6R-BH4 may trigger some change in the mechanism of DA release. Thus we have conducted extensive investigations in order to clarify the molecular mechanism of DA release. As a result, we have discovered, in a membrane fraction of the brain, a receptor site which is saturated by 6R-BH4 and highly specific for 6R-BH4 with high affinity and hence is the possible regulatory site in the DA release mechanism. We have further found that because of said specificity, 6R-BH4 receptor is capable of strictly distinguishing 6R- and 6S-optical isomers of tetrahydrobiopterin and thus is capable of selectively recognizing the 6R-isomer. Thus, these characteristics of the receptor completely differ from those of certain known enzymes capable of recognizing 6R-BH4 as their coenzyme.

Accordingly, the present invention relates to a receptor specific for 6R-BH4.

The receptor of the present invention specifically reacts with 6R-BH4. Further, it is solubilized with CHAPS [3-{(3-cholamidopropyl)dimethylammonio}-1-propanesulfonate]. When it is heated at 100° C. for 10 minutes, the solubilized product loses most of its binding ability to 6R-BH4. When incubated with trypsin at 37° C. for 15 minutes, the solubilized product significantly loses its binding ability to 6R-BH4. The receptor has a relative molecular weight about 340 to 380 kilodaltons when a rat cerebellum specimen solubilized and labeled with [6-$^3$H]6R-BH4 is separated by a molecular sieve column on COSMOSIL 5 Diol-300 porous silica, 300 Å, and the radioactivity is measured. As a result of an analysis by SDS electrophoresis, it has a molecular weight of about 160 kilodaltons. The receptor of the present invention may exist as a molecular fragment specifically reactive to 6R-BH4.

The above-mentioned properties of the 6R-BH4 receptor according to the present invention are confirmed by the following methods.

Binding to 6R-BH4

The action as the receptor for 6R-BH4 can be confirmed by studying the ability to bind to 6R-BH4.

For example, fractions obtained by homogenizing various regions sections of rat brain or other organs can be suspended in an appropriate buffer solution, for example, 50 mM Tris hydrochloride (pH 7.4), 100 mM NaCl, 10 mM $MgCl_2$, 2 mM ascorbic acid and 6 mM cysteine, and incubated together with an appropriate amount of tritium-labeled 6(R)-L-erythro-5,6,7,8-tetrahydrobiopterin ([6-$^3$H] 6R-BH4) under appropriate conditions, for example, at 37° C. for 10 minutes. Next, the protein-bound fraction is separated by a glass filter and the radioactivity in this fraction is determined by a conventional method.

High affinity to 6R-BH4

The high affinity of the receptor to [6-$^3$H]6R-BH4 can be confirmed by Scatchard plot analysis.

The Scatchard plot analysis may be carried out, for example, as follows. In an appropriate buffer solution, for example, 50 mM Tris hydrochloride (pH 7.4), 100 mM NaCl, 10 mM $MgCl_2$, 2 mM ascorbic acid and 6 mM cysteine solution, a fraction containing the receptor solubilized with CHAPS is incubated with [6-$^3$H]6R-BH4 at various concentrations under appropriate conditions, for example, at 37° C. for 10 minutes. Then the radioactivity is measured by a conventional method and plotted. From the plots, Kd (dissociation constant) and Bmax are determined and employed as indicators of the affinity. The receptor according to the present invention shows an affinity exceeding those of known enzymes taking part in the 6R-BH4 biosynthesis or enzymes for which 6R-BH4 serves as a coenzyme.

Binding specificity to 6R-BH4

The specificity of the receptor of the present invention in binding to 6R-BH4 can be confirmed by a competitive binding test with the use of various compounds at varying concentrations.

In this method, the above-mentioned compounds at varying concentrations (for example, biopterin as will be described in Example 6 hereinafter) are added as a ligand simultaneously with [6-$^3$H]6R-BH4 to the reaction mixture and the reaction is performed. The ability of the receptor of the present invention to bind to 6R-BH4 will not be inhibited to any substantial extent by these ligands.

Characteristics as Protein

1) Inactivation Under Heating

A solution of a receptor fraction solubilized with CHAPS in 10 mM CHAPS and 50 mM Tris hydrochloride (pH 7.4) is subjected to treatment under heating at 100° C. for 10 minutes. Then the same binding test as the one described above is carried out to confirm disappearance of the binding ability.

2) Inactivation by Protease

To a solution of a receptor fraction solubilized with CHAPS in 10 mM CHAPS and 50 mM Tris hydrochloride (pH 7.4), 100 μg/ml of trypsin (Wako Pure Chemical Industries, Ltd.) is added and the mixture is incubated at 37° C. for 15 minutes. Next, the same binding test as the one described above is carried out in order to confirm disappearance of the binding ability.

3) Gel Filtration HPLC Analysis of Receptor Protein Labeled With [6-$^3$H]6R-BH4

In a solution of 100 mM calcium phosphate buffer, 100 mM NaCl, 10 mM $MgCl_2$, 2 mM ascorbic acid and 6 mM cysteine, a fraction of the receptor solubilized with CHAPS is incubated together with an appropriate amount of [6-$^3$H] 6R-BH4, in a reaction volume of 120 μl, at 37° C. for 10 minutes. The reaction mixture thus obtained is injected into HPLC under conditions as specified below.

Column: Cosmoseal 5 Diol-300 (7.5×300 mm),
Mobile phase: 100 mM potassium phosphate buffer solution, pH 7.4, 5 mM CHAPS, 0.1 mM ascorbic acid and 0.1 mM cysteine.
Flow rate: 1 ml/min.

The eluate is fractionated at the rate of 0.25 ml/15 sec/test tube. After adding 16 ml of creasol to each fraction, the radioactivity is measured in a liquid scintillation counter. Then the receptor peak is compared with molecular weight markers to confirm the relative molecular weight. In this HPLC analysis, the receptor of the present invention typically shows a single peak and a relative molecular weight of about 340 to 380 kilodaltons.

4) Analysis by SDS Electrophoresis

A receptor protein fraction from rat cerebellum, which has been solubilized by CHAPS and partially purified by molecular sieve column chromatography followed by 2',5'-ADP affinity column chromatography, is electrophoresed on an SDS polyacrylamide gel in a conventional manner and the separated bands are observed under silver-staining. Main bands are located around 50 to 60 kilodaltons and at around 160 kilodaltons. The bands at 50 to 60 kilodaltons are assignable to glutathione reductase and malic enzyme which have affinity to the 2',5'-ADP column but never bind to 6R-BH4. Thus the molecular species at 160 kilodaltons corresponds to the protein (receptor) which binds to 6R-BH4.

The 6R-BH4 receptor of the present invention can be extracted and purified from animals and plants, for example, tissues of mammals including humans or insects. Although the cerebellum which contains a large amount of the receptor of the present invention is particularly suitable isolation source thereof, there are a number of tissues containing this receptor, as will be shown in Example 4 hereinafter. Furthermore, the receptor of the present invention may occur as a fragment specifically reactive with 6R-BH4 in the molecules of certain bioproteins. It may, therefore, be possible to obtain the receptor from such proteins.

The 6R-BH4 receptor of the present invention can be prepared from an isolation source by any appropriate method without particular limitation. For example, an isolation source such as various regions of rat brain or other organs is homogenized and spun at about 1,000×g. The supernatant is centrifuged at about 17,000×g. The receptor of the present invention is contained in the precipitate (membrane fraction) and in the supernatant (cytosol fraction). The centrifugation may be repeated twice or more, if necessary. The receptor contained in the precipitate can be solubilized in the presence of an appropriate surfactant such as CHAPS, which can be separated by an appropriate means such as centrifugation to provide a solubilized product. It is possible to further purify the solubilized product, with the binding ability to 6R-BH4 as an indicator, by an appropriate combination of purification procedures such as a gel filtration, an ion exchange chromatography, the use of various adsorbents including immunoadsorbents and electrophoresis. A specific purification example will be given in Example 7 hereinafter.

The fraction which is specifically reactive with 6R-BH4 can be subjected to a digestion with a conventional protease such as lysyl endopeptidase or to treatment with a chemical substance such as cyanogen bromide whereby the receptor peptide fragment can be obtained. The peptide fragment may be further purified by, for example, HPLC. The fragment may be screened by a competitive binding test for 6R-BH4.

Alternatively, the receptor of the present invention can be obtained by the method comprising the steps of extracting messenger RNA (mRNA) from cells of an organ abounding in said receptor such as the cerebellum, the whole brain, heart, spleen, lung or adrenal glands by a conventional method; constructing a cDNA library from the mRNA; selecting a cDNA encoding the amino acid sequence of the target protein by screening the library by any of various procedures; inserting the cDNA thus selected into an expression vector in a conventional manner; transfecting said vector into appropriate host cells (animal cells); and then allowing expression of the protein. The above-mentioned selection of the cDNA can be conducted by, for example, inserting the cDNAs into a vector capable of functioning in animal cells, transfecting host animal cells with said vector and then detecting the target cDNA based on the specific binding between the receptor expressed on the surface of the host cells and 6R-BH4.

When the receptor of the present invention is to be obtained by genetic engineering techniques, not only a recombinant gene originating from the cDNA but also a synthetic DNA obtained by designing the nucleotide sequence based on the amino acid sequence which will be deduced by the cDNA may be used.

The receptor of the present invention is useful as a tool in studying biochemical cellular reactions in response to 6R-BH4 binding to the cells; as a tool in searching for and developing agonists of the 6R-BH4 actions on the central nervous and immunological systems or antagonists capable of interrupting these actions when said search and development are conducted on the basis of the biochemical cellular reactions in response to 6R-BH4 binding to the cells and various other natures concerning the binding ability of 6R-BH4; and also as a diagnostic or therapeutic drug for diseases which are attributable to 6R-BH4.

Particular examples of the diagnostic and therapeutic drugs include diagnostic drugs for diseases induced by shortage, decrease or increase in 6R-BH4 such as malignant phenylketonuria, Parkinson's disease, infantile autism, manic-depressive psychosis and Alzheimer's disease and therapeutic drugs for diseases in which the receptor can effectively induce pharmacological effects by the inhibitory action on the biochemical cellular reactions responsive to binding of 6R-BH4 to the receptor.

For these purposes, the receptor of the present invention can be used in various assay methods in a conventional manner taking advantage of the specific binding ability thereof to 6R-BH4. As examples of such assay methods are mentioned, assays on the basis of competition, for binding to a labeled 6R-BH4 standard, between the receptor of the invention and and samples (for example, biological samples such as plasma, autopsied brain and cerebrospinal fluid or candidates of an agonist or an antagonist), and specific binding tests between the receptor of the present invention and a labeled sample. In these assay procedures, the receptor of the present invention may be immobilized on a solid carrier in accordance with a conventional method.

The receptor of the present invention can be provided in the form of a kit to be used in the above-mentioned tests. The receptor may be provided in the form of either a solution, a freeze-dried product or an immobilized product on a solid carrier. Further, the kit may optionally contain a labeled 6R-BH4 standard and other components required in the assay such as a buffer commonly used for diluting samples, a buffer for diluting various reagents and a washing liquid.

The following examples are provided to further illustrate the present invention. However, it is to be understood that the present invention is not limited thereto.

EXAMPLE 1

Production of Tritium-Labeled 6R-BH4

In accordance with the following reaction scheme, tritium-labeled 6R-BH4 (hereinafter referred to as [6-$^3$H]6R-BH4) was prepared.

Tritium was introduced to the 6-position of 7,8-dihydrobiopterin (I) via a reduction reaction with NaB[$^3$H]$_4$. Then proton was introduced into the 5-position by a water-quenching reaction to give [6-$^3$H]6R-BH4 (II).

(I) 7,8-dihydrobiopterin (II) 5,6,7,8-tetrahydrobiopterin

The obtained racemic mixture was purified by HPLC and the target [6-$^3$H]6R-BH4 was separated from [6-$^3$H]6S-BH4. FIG. 1 shows an UV chromatogram (265 nm) of the standard sample. The results shown in FIG. 2 indicate that the radiochemical purity of the [6-$^3$H]6R-BH4 final product was 98% or higher.

EXAMPLE 2

Preparation of P2 Fraction and Cytosol Fraction

By using various regions of rat brain and other organs as starting materials, fractions containing 6R-BH4 receptor were prepared in the following manner.

The starting material was homogenized in 10 volumes of 0.32M sucrose solution and then centrifuged (1,000×g, 12 minutes). The supernatant was separated and further centrifuged at a high speed (17,000×g, 30 minutes). The precipitate was suspended in 10 volumes of 50 mM Tris hydrochloride (pH 7.4). The obtained suspension was further centrifuged (17,000×g, 10 minutes) and the precipitate thus obtained was suspended again in 10 volumes of 50 mM Tris hydrochloride (pH 7.4). The suspension thus obtained was referred to as P2 fraction.

The starting material was homogenized in 10 volumes of 0.32M sucrose solution and then centrifuged (1,000×g, 12 minutes). The supernatant was separated and further centrifuged at a high speed (17,000×g, 30 minutes). The supernatant was further centrifuged (100,000×g, 60 minutes) and the supernatant thus obtained was referred to as the cytosol fraction.

EXAMPLE 3

Preparation of Solubilized Fraction

By using various regions of rat brain and other organs as a starting material, a solubilized fraction containing 6R-BH4 receptor was prepared in the following manner.

The starting material was homogenized in 10 volumes of 0.32M sucrose solution and then centrifuged (1,000×g, 12 minutes). The supernatant was separated and further centrifuged at a high speed (17,000×g, 30 minutes). The precipitate was suspended in 10 volumes of 50 mM Tris hydrochloride (pH 7.4). The suspension was further centrifuged (17,000×g, 10 minutes) and the precipitate thus obtained was suspended in 5 volumes of 5 mM CHAPS and 50 mM Tris hydrochloride (pH 7.4). The suspension was stirred in a refrigerated room for 1 hour and then ultracentrifuged (100,000×g, 60 minutes). The supernatant thus obtained was referred to as the solubilized fraction.

EXAMPLE 4

Binding of 6R-BH4 to P2 and Cytosol Fractions

The ability of [6-$^3$H]6R-BH4 to bind to P2 and cytosol fractions prepared in Example 2 was determined. As a result, it was confirmed that 6R-BH4 receptor was contained in P2 fraction and cytosol fraction derived from all of the tested brain regions and organs.

METHOD

In a suspension of 50 mM Tris hydrochloride (pH 7.4), 100 mM NaCl, 10 mM MgCl$_2$, 2 mM ascorbic acid and 6 mM cysteine, P2 fraction was incubated with 20 nM [6-$^3$H] 6R-BH4 at 37° C. for 10 minutes in a reaction volume of 200 µl or 400 µl. Then the reaction was ceased by adding 4 ml of ice-cooled 50 mM Tris hydrochloride (pH 7.4) and 100 mM NaCl.

Then the mixture was passed through a glass filter. After being washed 4 times with 4 ml portions of 50 mM Tris hydrochloride (pH 7.4) and 100 mM NaCl, the filter was taken off and filled with 2 ml of ethanol and 8 ml of creasol (Nacalai Tesque). Then the radioactivity on the filter was measured in a liquid scintillation counter.

Figure 1:
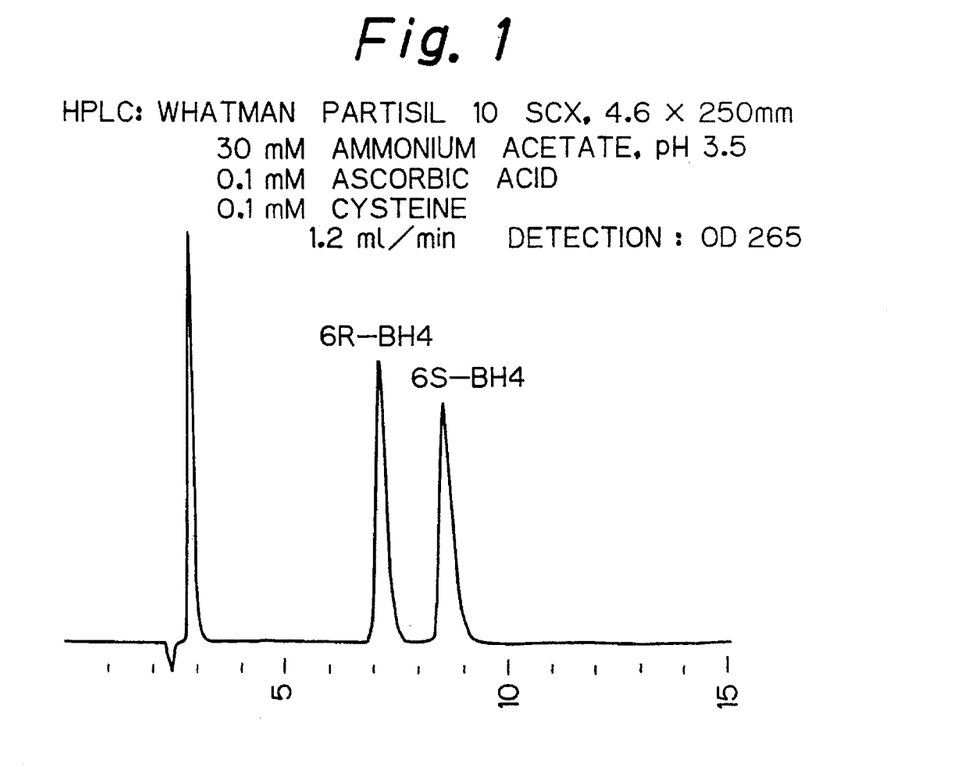
FIG. 1 is an HPLC chromatogram of standard samples provided for identification of the labeled compound shown in FIG. 2.
Figure 2:
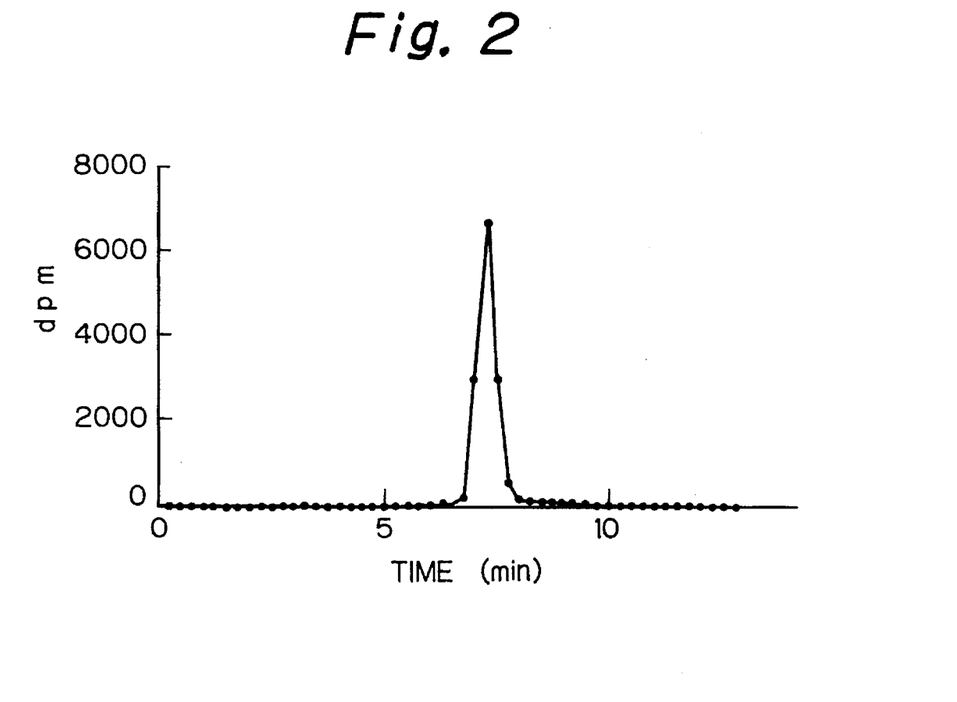
FIG. 2 is an HPLC chromatogram carried out for confirming the radiochemical purity of the purified synthetic [6-$^3$H]6R-BH4, i.e., a specimen finally employed in the binding test.
Figure 3A:
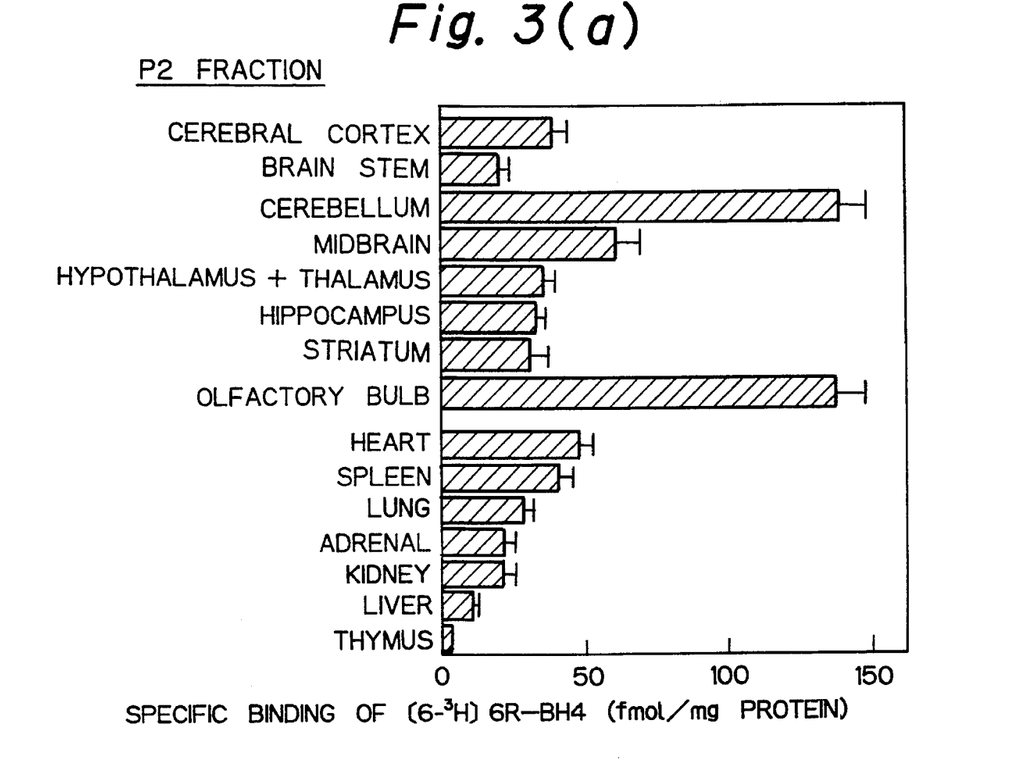
FIGS. 3a and 3b are graphs showing the binding abilities of fractions prepared from various regions of rat brain and other tissues, wherein (a) shows the results of P2 fraction and (b) shows the results of cytosol fraction.
Figure 3B:
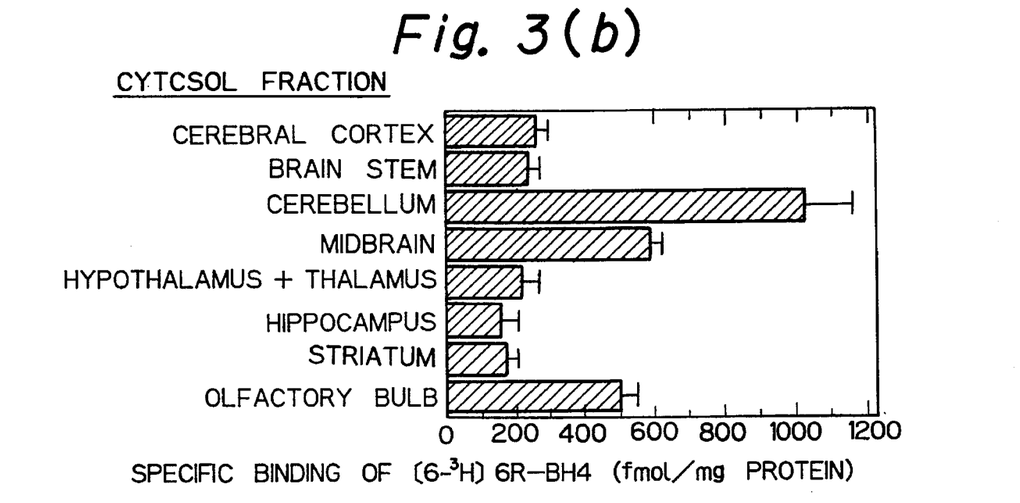

FIG. 3 shows the results in terms of "mean±standard deviation (S.D.)" (n=4). The specific binding represents the binding wherein the nonspecific binding as determined by reacting 10 µM of 6R-BH4 and [6-$^3$H]6R-BH4 has been subtracted.

FIG. 3 clearly indicates that the fractions derived from cerebellum showed higher levels of binding. Thus, the following description will be made by referring to P2 fraction and CHAPS-solubilized fractions from cerebellum.

In the case of cytosol fraction, the fraction was incubated in the solution of the same composition as the above-mentioned one employed for P2 fraction at 37° C. for 10 minutes. Then 3 mg/ml (final concentration) of bovine γ-globulin and 15% (final concentration) of polyethylene glycol 6000 were added to cease the reaction.

Next, the reaction mixture was cooled on ice for 10 minutes and then passed through a glass filter. After being washed 4 times with 4 ml portions of 8% polyethylene glycol and 10 mM Tris hydrochloride (pH 7.4), the filter was taken off and placed in a vial. 2 ml of ethanol and 8 ml of creasol (Nacalai Tesque) were added to the filter and the radioactivity on the filter was measured in a liquid scintillation counter.

The distribution of 6R-BH4 receptor in the brain cytosol fraction was similar to that of the P2 fraction.

EXAMPLE 5

Scatchard Plot Analysis

By using a determined amount of the solubilized fraction of rat cerebellum, Scatchard plot analysis with regard to the solubilized receptor protein of the present invention was performed by the conventional method. The following data was obtained: Kd (dissociation constant)=21 nM, Bmax (maximum binding constant)=550 fmol/mg protein. The Kd value thus obtained was greater than those (several ten µM) of any known enzymes which participate in the biosynthesis of 6R-BH4 or enzymes for which 6R-BH4 acts as a coenzyme. Thus it was confirmed that the receptor according to the present invention was a completely novel one.

METHOD

About 0.6 mg (protein) of the solubilized fraction obtained in Example 3 was incubated together with [6-$^3$H] 6R-BH4 at various concentrations in a 400 µl solution of 50 mM Tris hydrochloride (pH 7.4), 100 mM NaCl, 10 mM MgCl$_2$, 2 mM ascorbic acid and 6 mM cysteine at 37° C. for 10 minutes. Then, 3 mg/ml (final concentration) of bovine γ-globulin and 15% (final concentration) of polyethylene glycol 6000 were added to cease the reaction.

The reaction mixture was cooled on ice for 10 minutes and then filtered through a glass filter. After being washed 4 times with 4 ml portions of 8% polyethylene glycol and 10 mM Tris hydrochloride (pH 7.4), the filter was taken off and placed in a vial. 2 ml of ethanol and 8 ml of creasol (Nacalai Tesque) were added to the filter and the radioactivity on the filter was measured in a liquid scintillation counter.

Figure 4:
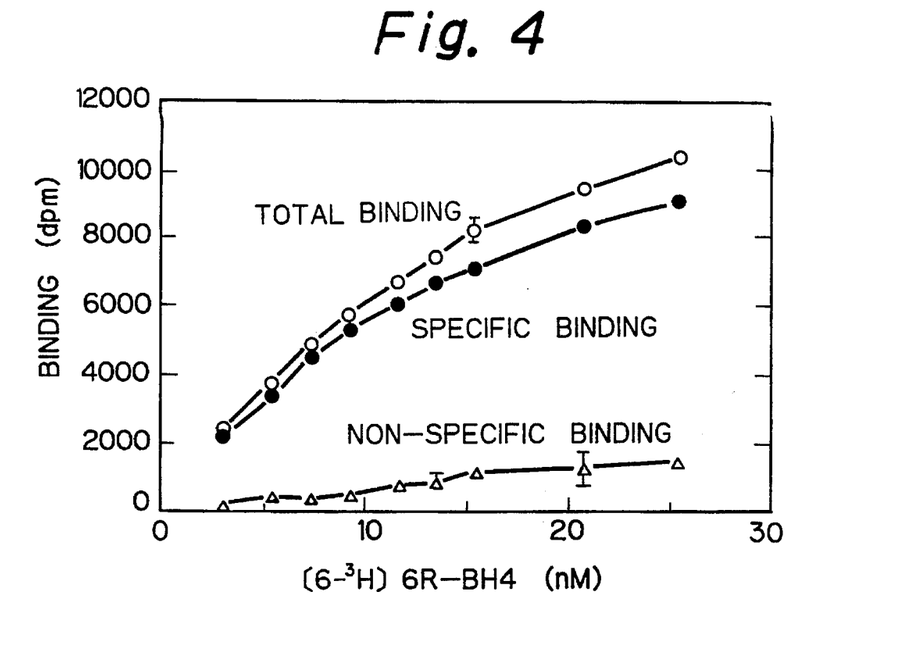
FIG. 4 is a graph showing the radioactivities which bound to the receptor when [6-$^3$H]6R-BH4 was added at various concentrations to a determined amount of the solubilized receptor.
Figure 5:
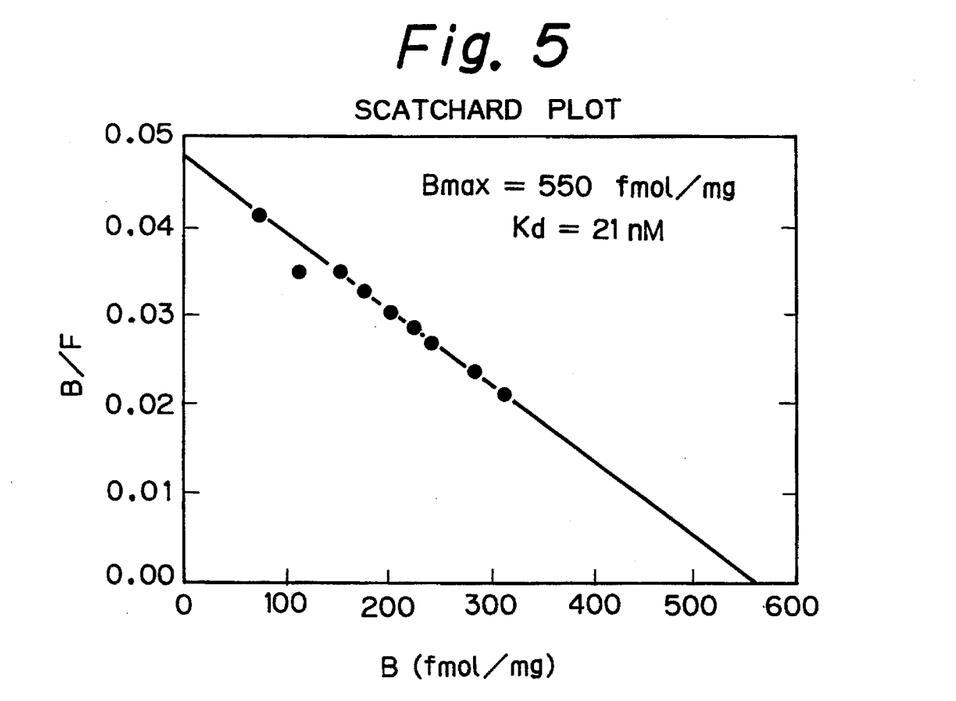
FIG. 5 is a graph drawn by Scatchard-plot analysis of the data of the specific binding shown in FIG. 4.

The results are shown in FIGS. 4 and 5. FIG. 4 is a graph showing the radioactivities which bound to the receptor when [6-$^3$H]6R-BH4 was added at various concentrations to a determined amount of the solubilized receptor. In FIG. 4, these radioactivities are referred to as the total binding, while nonspecific binding indicates radioactivities measured by adding 10 µM of unlabeled 6R-BH4 simultaneously with [6-$^3$H]6R-BH4 at various concentrations. Accordingly, the saturation of the specific binding can be calculated as the difference between the total and nonspecific bindings. FIG. 5 is a graph drawn by Scatchard plot analysis of the data of the specific binding in FIG. 4.

EXAMPLE 6

Binding Specificity

By using the solubilized fraction of rat cerebellum, a competitive binding test between various compounds at varying concentrations and 13 nM of [6-$^3$H]6R-BH4 was carried out. As a result, it was found that the receptor of the present invention is specific for 6R-BH4.

IC$_{50}$ data indicated that the affinity of the receptor of the present invention to 6R-BH4 was more than 50 times and 1,000 times as high as its affinities to 7,8-dihydrobiopterin (BH2) and 6S-BH4, respectively. This is a point of great difference from the previous knowledge that the coenzyme activity of 6R-BH4 for aromatic amino acid hydroxylases is maintained relatively well even if 6R-BH4 is converted to 6S-BH4.

These results also support the fact that the receptor of the present invention is specific for 6R-BH4. In addition, since this receptor does not show any substantial binding ability to tetrahydrofolic acid (FAH4), it completely differs From various known folic acid-binding proteins occurring in vivo.

METHOD

About 0.3 mg (protein) of the solubilized fraction obtained in Example 3 was incubated together with 13 nM of [6-$^3$H]6R-BH4 in a 200 μl solution of 50 mM Tris hydrochloride (pH 7.4), 100 mM NaCl, 10 mM MgCl$_2$, 2 mM ascorbic acid and 6 mM cysteine at 37° C. for 10 minutes. Then 3 mg/ml (final concentration) of bovine γ-globulin and 15% (final concentration) of polyethylene glycol 6000 were added to cease the reaction.

Next, the reaction mixture was cooled on ice for 10 minutes and then passed through a glass filter. After being washed 4 times with 4 ml portions of 8% polyethylene glycol and 10 mM Tris hydrochloride (pH 7.4), the filter was taken off and placed in a vial. 2 ml of ethanol and 8 ml of creasol (Nacalai Tesque) were added to the filter and the radioactivity on the filter was measured in a liquid scintillation counter.

Figure 6:
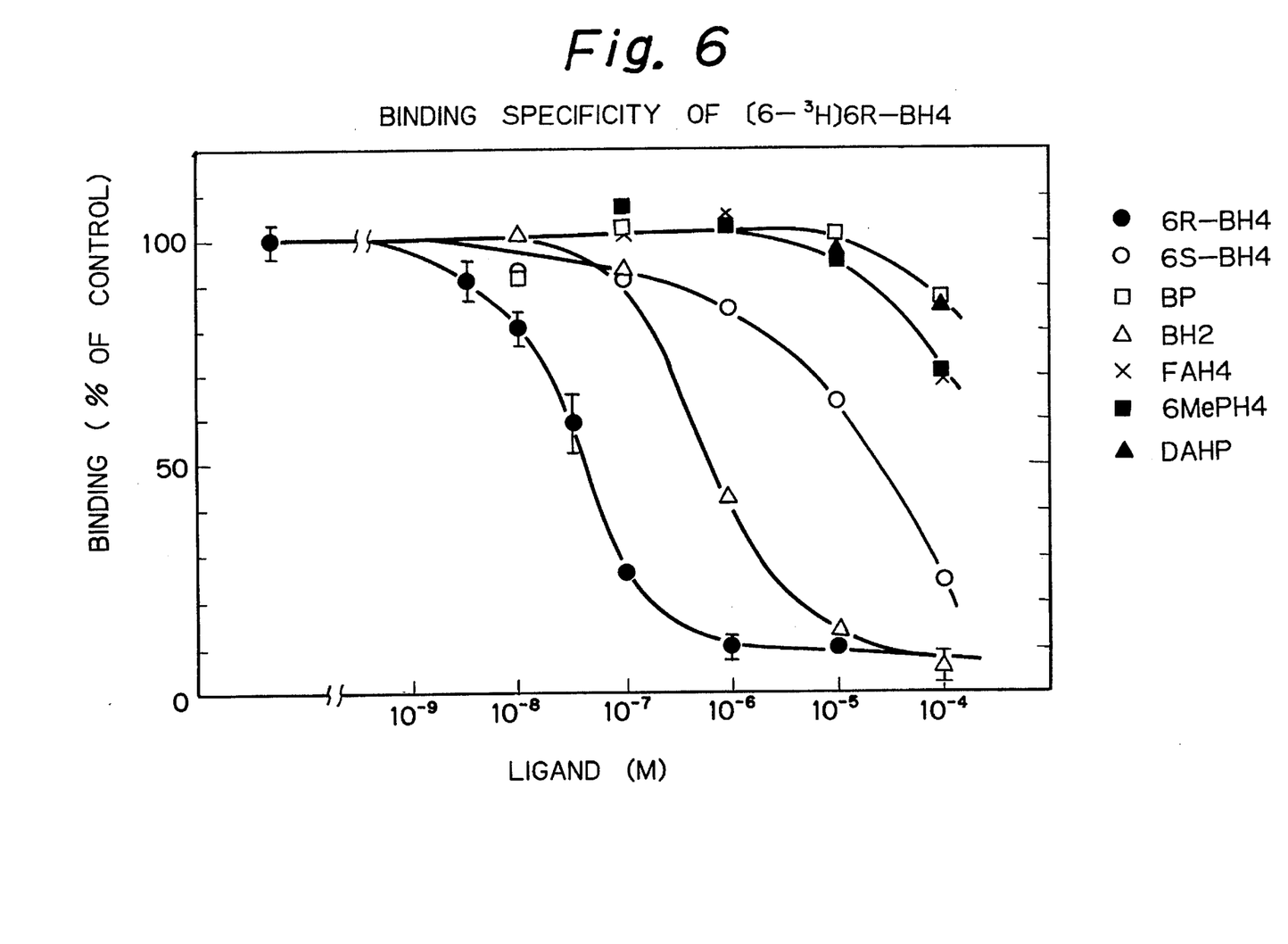
FIG. 6 is a graph showing that the receptor of the present invention has a specific binding ability to 6R-BH4.

The results thus obtained were referred to as total binding. Then various compounds at varying concentrations were added as a ligand simultaneously with [6-$^3$H]6R-BH4 in the above procedure, and the reaction was effected. FIG. 6 shows the results, wherein BP represents biopterin, 6MePH4 represents 6-methyl-5,6,7,8-tetrahydropterin and DAHP represents 2,4-diamino-6-hydroxypyrimidine (a potential inhibitor for GTP cyclohydrolase, i.e., 6R-BH4 synthetase).

EXAMPLE 7

Characteristics as a Protein

1) Inactivation Under Heating

A solution of the solubilized fraction prepared in Example 3 in 10 mM CHAPS and 50 mM Tris hydrochloride (pH 7.4) was heated at 100° C. for 10 minutes. Then the same binding test as the one described above was carried out and the binding abilities were compared. As a result, most part (98%) of the binding ability of the solubilized protein to [6-$^3$H]6R-BH4 disappeared.

2) Inactivation by Protease

To a solution of the solubilized fraction in 10 mM CHAPS and 50 mM Tris hydrochloride (pH 7.4), 100 μg/ml of trypsin (Wako Pure Chemical Industries, Ltd.) was added and the mixture was incubated at 37° C. for 15 minutes. Then the same binding test as the one described above was carried out and the binding abilities were compared. As a result, the binding ability of the solubilized protein to [6-$^3$H]6R-BH4 significantly disappeared.

3) Gel Filtration HPLC Analysis of Receptor Protein Labeled with [6-$^3$H]6R-BH4

Figure 7:
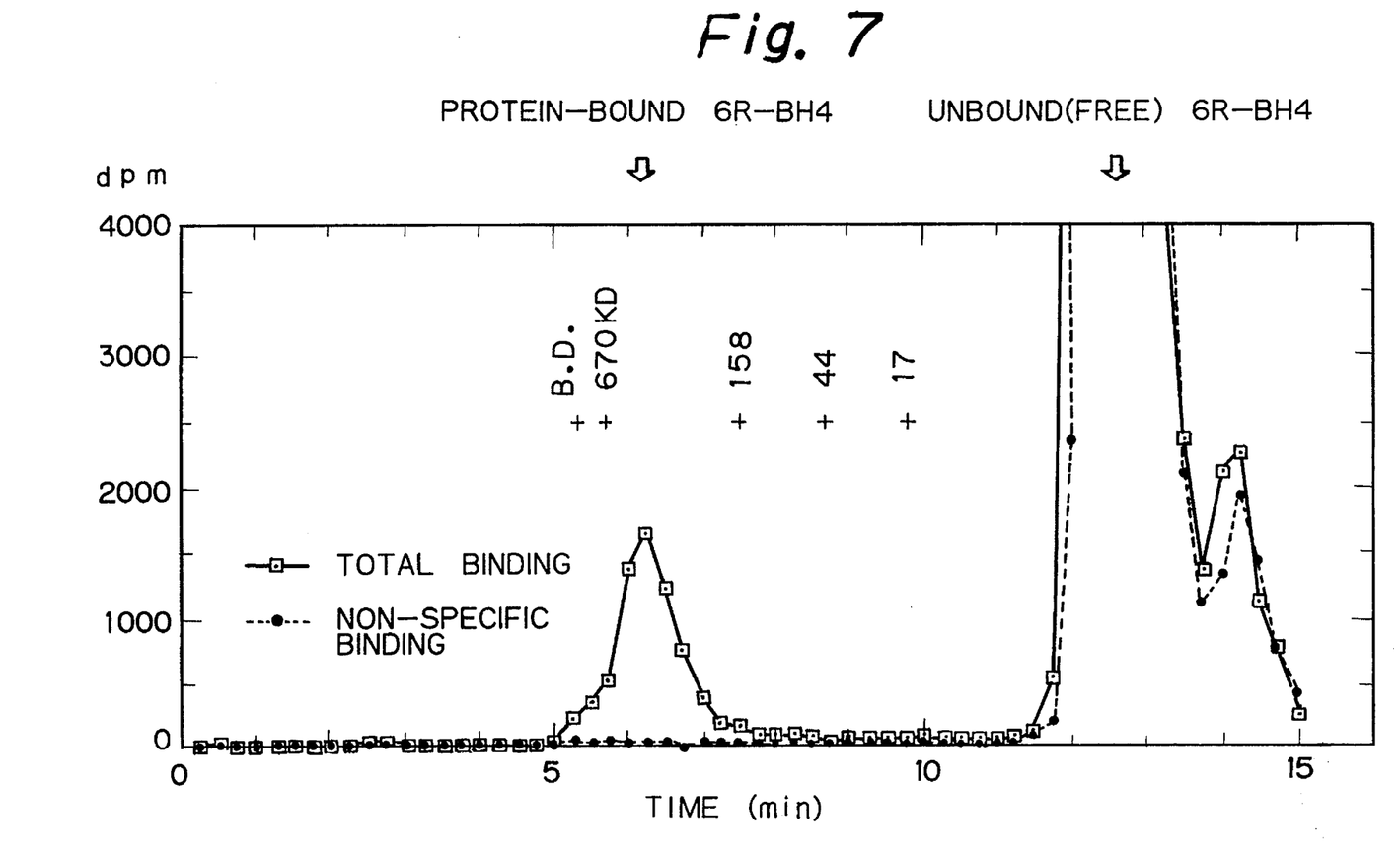
FIG. 7 is a gel filtration chromatogram of the solubilized fraction containing the receptor of the present invention.

As the result of an analysis with the use of a molecular sieve on Cosmoseal 5 Diol-300 (Nacalai Tesque) column (refer to FIG. 7), [6-$^3$H]6R-BH4 which had been bound to the receptor protein was detected at a position around 340 to 380 kilodaltons between molecular markers thyroglobulin (670 kilodaltons) and γ-globulin (158 kilodaltons). The last peaks seen in FIG. 7 are considered to be assignable to unbound free [6-$^3$H]6R-BH4 and $^3$H$_2$O formed during the treatment.

About 0.2 mg (protein) of the solubilized fraction obtained in Example 3 was incubated together with about 360,000 dpm of [6-$^3$H]6R-BH4 in a 120 μl solution of 100 mM potassium phosphate buffer (pH 7.4), 100 mM NaCl, 10 mM MgCl$_2$, 2 mM ascorbic acid and 6 mM cysteine at 37° C. for 10 minutes.

100 μl of the reaction product was injected into HPLC under the conditions as specified below.
Column: COSMOSIL 5 Diol-300 (7.5×300 mm).
Mobile phase: 100 mM potassium phosphate buffer solution, pH 7.4, 5 mM CHAPS, 0.1 mM ascorbic acid and 0.1 mM cysteine.
Flow rate: 1 ml/min.

The eluate was fractionated at the rate of 0.25 ml/15 sec/test tube. After adding 16 ml of creasol to each fraction, the radioactivity was measured in a liquid scintillation counter. FIG. 7 shows the results.

Then the cytosol fraction was analyzed by the same method, and similar results as the one described above were obtained.

4) Analysis by SDS Electrophoresis

Cerebellum fraction of a rat was solubilized with CHAPS and purified with the above-mentioned COSMOSIL 5 Diol-300 column. Then the active fraction was further purified by using a 2',5'-ADP column (Pharmacia). From fractions showing high [6-$^3$H]6R-BH4 binding activities, about 3 μg of total protein was taken out and electrophoresed on an SDS-PAG plate 4/20 (Daiichi Kagaku) and silver stained (Wako Pure Chemical Industries, Ltd.). As a result, main bands were located around 50 to 60 kilodaltons and at about 160 kilodaltons. The bands at 50 to 60 kilodaltons were assignable to glutathione reductase and malic enzyme which have affinity to 2',5'-ADP column but would never bind to 6R-BH4. Thus the molecular species at 160 kilodaltons corresponded to the 6R-BH4-binding protein (receptor).

We claim:

1. An isolated and purified 6(R)-L-erythro-5,6,7,8-tetrahydrobiopterin (6R-BH4) receptor which specifically binds to 6R-BH4 and which is contained in the cytosol fraction obtained from a homogenate of an animal organ or in the membrane fraction obtained from a homogenate of an animal organ and which is capable of being solubilized from the membrane fraction in the presence of 3-{(3-cholamidopropyl)dimethylammonio}-1-propanesulfonate (CHAPS), characterized in that the binding ability thereof to bind to 6R-BH4 is mostly lost by heating at 100° C. for 10 minutes, the binding ability thereof to bind to 6R-BH4 is significantly lost by incubating with trypsin at 37° C. for 15 minutes, and said receptor shows substantially a single peak at about 340 to 380 kilodaltons when said receptor is solubilized from the membrane fraction in the presence of CHAPS and is specifically bound to tritium-labeled 6R-BH4 and is subjected to gel filtration chromatography.

2. The receptor of claim 1, wherein the binding of the receptor to 6(R)-L-erythro-5,6,7,8-tetrahydrobiopterin is between 50 to 1000 times greater than the binding of the receptor to 7,8-dihydrobiopterin or 6(S)-L-erythro-5,6,7,8-tetrahydrobiopterin.

3. An isolated and purified protein which is contained in the cytosol fraction or in the membrane fraction obtained from a homogenate of an animal organ and has a selective binding affinity to 6R-BH4, characterized in that the binding ability thereof to bind to 6R-BH4 is mostly lost by heating at 100° C. for 10 minutes, the binding ability thereof to bind to 6R-BH4 is significantly lost by incubating with trypsin at 37° C. for 15 minutes, and said protein shows substantially a single peak at about 340 to 380 kilodaltons when said protein is solubilized from the membrane fraction in the presence of CHAPS and specifically bound to tritium-labeled 6R-BH4 and subjected to gel filtration chromatography.

4. The protein of claim 3, wherein the binding of the protein to 6(R)-L-erythro-5,6,7,8-tetrahydrobiopterin is between 50 to 1000 times greater than the binding of the protein to 7,8-dihydrobiopterin or 6(S)-L-erythro-5,6,7,8-tetrahydrobiopterin.

* * * * *